United States Patent
Van Dyke et al.

(10) Patent No.: US 10,400,019 B2
(45) Date of Patent: Sep. 3, 2019

(54) KERATIN NANOMATERIALS AND METHODS OF PRODUCTION

(71) Applicants: Mark Van Dyke, Blacksburg, VA (US); Maria Rahmany, Paramus, NJ (US)

(72) Inventors: Mark Van Dyke, Blacksburg, VA (US); Maria Rahmany, Paramus, NJ (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 147 days.

(21) Appl. No.: 15/308,285

(22) PCT Filed: May 1, 2015

(86) PCT No.: PCT/US2015/028893
§ 371 (c)(1),
(2) Date: Nov. 1, 2016

(87) PCT Pub. No.: WO2015/168622
PCT Pub. Date: Nov. 5, 2015

(65) Prior Publication Data
US 2017/0051027 A1    Feb. 23, 2017

Related U.S. Application Data

(60) Provisional application No. 61/987,182, filed on May 1, 2014, provisional application No. 61/987,855, filed on May 2, 2014.

(51) Int. Cl.
| | |
|---|---|
| *B82Y 5/00* | (2011.01) |
| *C07K 1/34* | (2006.01) |
| *A61L 15/32* | (2006.01) |
| *A61L 24/10* | (2006.01) |
| *A61L 26/00* | (2006.01) |
| *A61L 27/22* | (2006.01) |
| *C07K 14/47* | (2006.01) |

(52) U.S. Cl.
CPC .......... *C07K 14/4741* (2013.01); *A61L 15/32* (2013.01); *A61L 24/108* (2013.01); *A61L 26/0047* (2013.01); *A61L 27/227* (2013.01); *B82Y 5/00* (2013.01); *C07K 1/34* (2013.01); *A61L 2400/12* (2013.01)

(58) Field of Classification Search
None
See application file for complete search history.

(56) References Cited

U.S. PATENT DOCUMENTS

2005/0124797 A1 * 6/2005 Kelly ................. C07K 14/4741
530/357

OTHER PUBLICATIONS

Hatzfeld and Franke, "Formation In Vitro of Heterotypic Complexes and Intermediate-sized Filaments by Homologous and Heterologous Recombinations of Purified Polypeptides", The Journal of Cell Biology 101: 1826-1841 (Nov. 1985) (Year: 1985).*
Herrman et al., "Characterization of Early Assembly Intermediates of Recombinant Human Keratins", Journal of Structural Biology 137: 82-96 (2002) (Year: 2002).*

* cited by examiner

*Primary Examiner* — Anand U Desai
(74) *Attorney, Agent, or Firm* — Keith A. Vogt; Vogt IP

(57) ABSTRACT

The present disclosure relates to keratin nanomaterials, methods for obtaining keratin nanomaterials, and biomaterials made from keratin nanomaterials. In particular, keratin nanomaterials comprising Type I and Type II monomer pairs are disclosed as well as a method for obtaining keratin nanomaterials comprising obtaining a solution of keratin and processing the solution by ultrafiltration with buffer solution containing phosphate.

22 Claims, 5 Drawing Sheets

KERATIN NANOMATERIALS AND METHODS OF PRODUCTION

CROSS-REFERENCE TO RELATED APPLICATIONS

This application claims priority to and the benefit of the filing dates of U.S. Provisional Application No. 61/987,182, filed May 1, 2014 and U.S. Provisional Application No. 61/987,855, filed May 2, 2014, the disclosures of which are hereby incorporated by reference herein in their entireties.

FIELD OF THE INVENTION

This disclosure relates generally to the field of keratin nanomaterials, biomaterials comprising keratin nanomaterials, and methods of producing keratin nanomaterials. More particularly, the instant disclosure relates to the production and use of keratin nanomaterials, which are macromolecular keratin complexes comprising dimers and tetramers of tightly associated keratin monomers.

BACKGROUND OF THE INVENTION

Intermediate filaments (IF) comprise assemblies of subunits belonging to a superfamily of α-helical proteins that fall into one of six major classes. Typically, IF proteins have common secondary structural characteristics that can generally be described as a monomeric form containing a central α-helical domain and head and tail globular domains. The central α-helical domain in IF proteins is highly conserved, with variation coming largely from differences in primary structure in the head and tail domains. In order to form intermediate filaments, these monomeric species polymerize to form elongated macromolecular complexes with a highly ordered superstructure. Two primary IF proteins include acidic and basic keratins (Type I and Type II IF protein classes respectively). Type I and Type II keratin monomers are generally expressed in epithelial cells and neither Type I nor Type II keratin monomers are able to assemble into a keratin filament on its own. Type I and Type II keratin monomers generally associate in a 1:1 ratio to form heterodimers, which further associate to assemble into heteropolymeric keratin filaments.

Keratin IF proteins can be further described as being from the "soft" epithelial sub-family or from the "hard" trichocytic sub-family. Approximately 20 keratins, also known as cytokeratins, are from the "soft" sub-family and consist of intracellular proteins making up cytoskeletal elements in epithelial cells. About 17 keratins are known to belong to the "hard" trichocytic sub-family, and these keratins make up structural appendages such as hooves, fingernails, fur, feathers, and hair fibers.

Research has shown that the process of protein self-assembly is highly sensitive to changes in the macromolecular complexes, namely dimers and tetramers. Moreover, the mere presence of damaged fragments of proteins can interfere with the self-assembly process and/or disrupt superstructure that has already formed—such holds true for keratin proteins as well. Keratin monomers form particularly strong macromolecular complexes, especially at the dimer and tetramer level, which are not easily denatured or broken down into their monomeric units. The problem in denaturing these complexes, however, is that the chemical methods used to break apart the keratin superstructure, primarily disulfide bonds, and the subsequent protein solubilization techniques, can result in significant damage to the keratin monomers. This damage often goes undetected and is detrimental to the formation, properties, and performance of keratin biomaterials. Recombinant keratins have yet to offer any promising alternatives to the field of keratin biomaterials as recombinant keratins are currently difficult and expensive to produce. To date, the entirety of keratin biomaterials technology has been based on extracting keratins from tissues such as hair fibers, wool, feathers and the like.

Previously described keratin biomaterials are made from keratin monomers, typically in the range of 40-60 kilo Daltons (kDa) and do not disclose the use of a purified keratin nanomaterial. Rouse J G, Van Dyke M E. A review of keratin-based biomaterials for biomedical applications. Materials 2010; 3:999-1014; Van Dyke M E. Hydrogel with controllable mechanical, chemical, and biological properties and method for making same. U.S. Pat. No. 7,001,987. Feb. 21, 2006; Van Dyke M E, Saul J M, Smith T L, de Guzman R. Controlled delivery system. U.S. Pat. App. Pub. No.: 2011/0217356. Filed Mar. 7, 2011. As described herein, a purified keratin nanomaterial includes keratins essentially devoid of structural damage and defects as well as damaged proteins and peptides that are associated with (i.e., attached to, bound to, etc.) the keratin nanomaterial.

Further still, the methods describing the keratin used in the manufacture of previously described keratin biomaterials yield molecular complexes that are not pure keratin nanomaterials. Even previously described "purified keratins" contain keratin complexes with tightly associated, damaged proteins, and protein fragments (i.e., peptides) that are detrimental to the self-assembly process, and/or can destabilize the biomaterial superstructure after its formation. Van Dyke M E. Wound healing compositions containing keratin biomaterials. U.S. Pat. No. 8,273,702. Sep. 25, 2012.

Keratins have been extracted from human hair fibers by oxidation or reduction using methods that are well known to those skilled in the art (see for example, Crewther, W. G., et al., The Chemistry of Keratins. Anfinsen, C. B., Jr., et al., editors. Advances in Protein Chemistry 1965, Academic Press. New York: 191-346). This chapter in *Advances in Protein Chemistry* contains references to more than 640 published studies on keratins and describes methods for extracting keratins. The methods described typically employ a two-step process whereby the cross-linked structure of keratins is broken down by either oxidation or reduction. If an oxidative treatment is used, the resulting keratins are referred to as keratoses and if a reductive treatment is used, the resulting keratins are referred to as kerateines. In these reactions, the disulfide bonds in cystine amino acid residues are cleaved, rendering the keratins soluble. As many of the keratins remain trapped within the protective structure of the cuticle, a second-step using a denaturing solution is typically employed to effect efficient extraction of the cortical proteins. Alternatively, in the case of reduction reactions, these steps can be combined or solutions, such as urea, thiourea, phosphates, diphosphates, sulfates, disulfates, cyanates, thiocyanates, carbonates, bicarbonates, transition metal hydroxides, surfactant solutions, and/or combinations thereof can be used (e.g., aqueous solutions of tris(hydroxymethyl)aminomethane in concentrations between 0.1 and 1.0M, and urea solutions between 0.1 and 10M).

The literature further characterizes that crude extracts of keratose and kerateines can be further refined into α-keratose, γ-keratose, acidic α-keratose, basic α-keratose, acidic γ-keratose, basic γ-keratose, α-kerateine, γ-kerateine, acidic α-kerateine, basic α-kerateine, acidic γ-kerateine, basic γ-kerateine, and keratin associated protein (KAP) fractions by a variety of methods such as isoelectric precipitation, ultrafiltration, chromatography, and combinations thereof. In a crude extract, the alpha fraction begins to precipitate below pH 6 and is essentially completely precipitated by pH 4.2. The KAP fraction generally co-precipitates with the alpha fraction, thereby producing an alpha/KAP mixture. The gamma fraction remains in solution, but can be precipitated by addition of a non-solvent. Non-solvents are water miscible but do not dissolve keratins (e.g., ethanol). Precipitation of the gamma fraction can be aided by cooling the ethanol and adding the keratin solution drop wise, rather than adding the ethanol to the keratin. Such fractionation procedures have been described in the literature and are known to those skilled in the art; however, these methods cannot yield the keratin nanomaterials described herein.

Further, many protein purification techniques are known in the art and range from fractional precipitation to immunoaffinity chromatography (for extensive treatment of this subject, see Scopes R. K. (editor). Protein purification: Principles and Practice ($3^{rd}$ ed. Springer, New York. 1993); Roe S., Protein purification techniques: A practical approach. ($2^{nd}$ ed. Oxford University Press, New York. 2001); or Hatti-Kaul R. and Mattiasson B., Isolation and purification of proteins. (Marcel Dekker AG, New York. 2003), incorporated herein by reference. For example, subfamilies of acidic and basic keratins have been described by Crewther et al. as being separable by moving bounding electrophoresis, but these fractions or their properties have not been extensively described (see Crewther (1965)). Separation techniques have been applied to keratin fractions such that they can be separated into sub-fractions with useful properties, and can be re-combined into "meta keratins" with properties that are different than the starting mixtures (see Richter J. R., et al. Structure-property relationships of meta-kerateine biomaterials derived from human hair. Acta Biomater. 2012; 8(1):274-81; Van Dyke, Mark E, et al. Keratin biomaterials for treatment of ischemia. U.S. Pat. No. 8,545,893. Oct. 1, 2013; and Nunez F, et al. Vasoactive properties of keratin-derived compounds. Microcirculation. 2011; 18(8):663-9). The gelation, binding of therapeutic compounds, mechanical, and chemical properties, and other characteristics of the resulting purified keratins are established in the literature; however, the extraction and purification techniques provided are not sufficient to provide keratins without damage and/or contaminants and provide the keratin nanomaterials described herein.

A need exists for keratin nanomaterials that are capable of self-assembly into biomaterials such as hydrogels, films, foams, coatings, and fibers as well as methods for keratin nanomaterials from keratin-containing sources.

Keratin nanomaterials are macromolecular complexes existing in the form of tightly associated dimers of Type I and Type II monomers, and/or tetramers formed from tight associations of two dimers. In nature, these macromolecular complexes are unstable and quickly polymerize to form higher ordered structures. Methods described in the prior art have failed to produce stable, purified keratin nanomaterials. Keratin nanomaterials remain tightly associated in the presence of strong denaturing solutions known in the art, for example, concentrated urea solutions. Keratin nanomaterials have chemical, physical and biological properties that are distinctly different from keratinous tissues found in nature including the source hair fibers, wool, feathers and the like, as well as previously described extracted and purified keratins. For example, keratinous tissues found in nature have an inert outer layer, referred to as the cuticle in the case of hair and fur fibers. Keratin nanomaterials are not inert and can, therefore, interact with other chemical compounds, solvents, cells and cell receptors, and the like. Moreover, biomaterials prepared from keratin nanomaterials have chemical, physical and biological properties that are distinctly different from conventional keratin biomaterials described in the prior art. For example, biomaterials prepared from keratin nanomaterials form stronger network structures, owning to their high degree of self-assembly, than do conventional keratin biomaterials. This property manifests itself in the ability of keratin nanomaterials to form hydrogels at lower keratin concentration, for example. In addition, biomaterials formed from keratin nanomaterials degrade more slowly than conventional keratin biomaterials, owning to the more highly ordered molecular structure, the stability of the molecular complex, and absence of damaged peptides that can serve as catalyst to degradation. Lastly, biomaterials made from keratin nanomaterials are less immunogenic, owning to the lack of damaged peptides and the intact native structure of the molecular complex of type I and type II monomers.

SUMMARY OF THE INVENTION

The subjects of the present disclosure are keratin nanomaterials, methods for producing the same, and biomaterials made from keratin nanomaterials. Keratins extracted from tissues such as wool, feathers, hair fibers, and the like are well known in the art; however, these methods result in complex mixtures of different keratin compounds. Even when sophisticated separation and purification steps are employed, the methods described in the prior art are able to produce, at best, keratins that are strongly complexed to damaged keratin molecules and remnants of keratin molecules such as peptide fragments. The methods disclosed in the prior art do not alter these tight interactions, and therefore, produce a chemical structure different from the subject keratin nanomaterials.

As such, conventional keratin biomaterials do not possess the same capability for self-assembly and do not result in the same network structures, or possess similar properties, including network structural stability, as keratin nanomaterials. We have recently discovered that only with controlled manipulation of the solution behavior of keratin extracts can keratin nanomaterials be obtained.

The processes described herein are effective at breaking these tight interactions and producing different chemical entities; namely, keratin nanomaterials. Biomaterials made from keratin nanomaterials such as gels, films, foams, sponges, scaffolds, fibers, putties, coatings, and particles have superior properties compared to conventional keratin biomaterials.

It is an object of the disclosure to provide one or more keratin nanomaterials, which are macromolecular keratin complexes comprising dimers and/or tetramers of tightly associated keratin monomers.

It is a further object of the disclosure to provide a method for producing one or more keratin nanomaterials.

It is still a further object of the disclosure to provide compositions comprising one or more of the keratin nanomaterials disclosed herein.

It is yet a further an object of the disclosure to provide one or more biomaterials comprising one or more of the keratin nanomaterials disclosed herein.

DETAILED DESCRIPTION

Definitions

Figure 1:
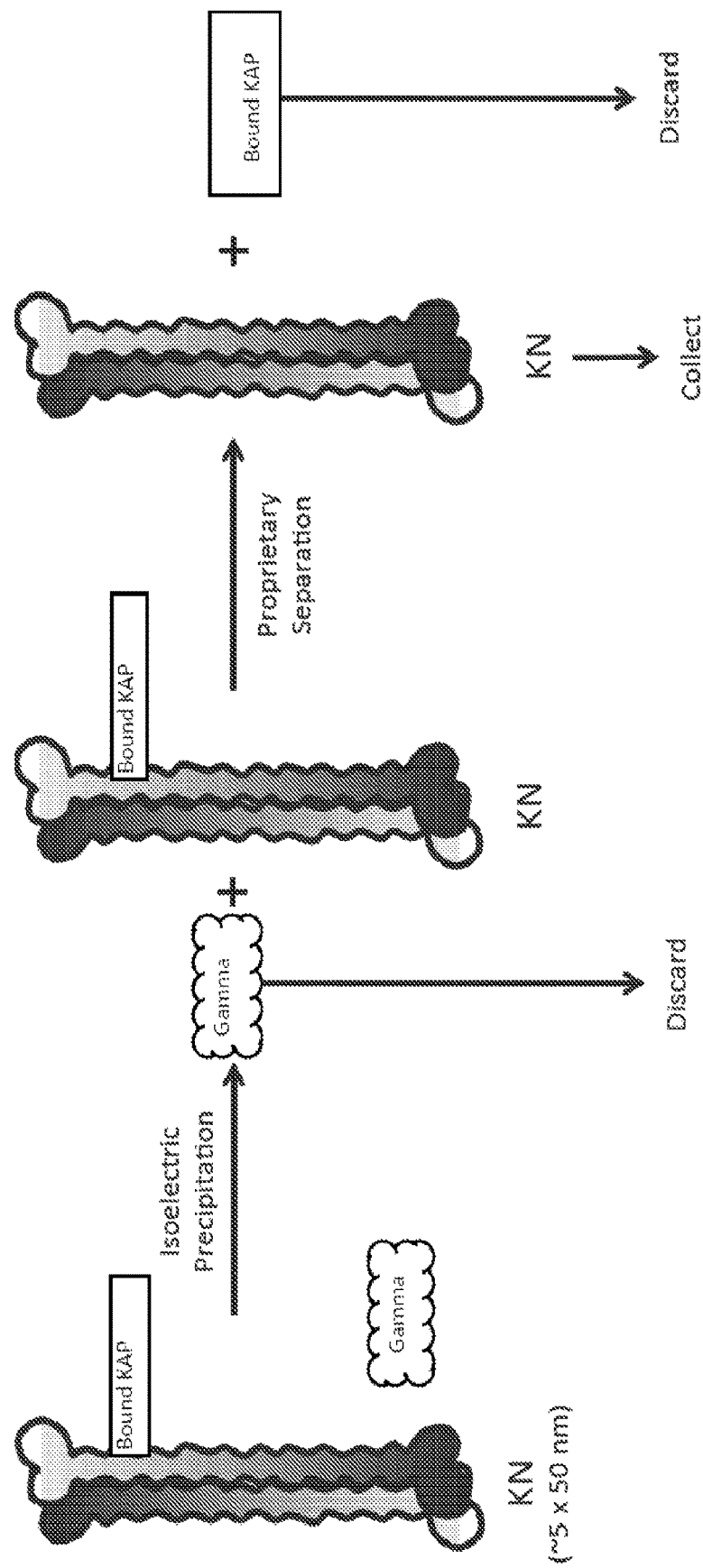
FIG. 1 is a schematic representation showing a keratin nanomaterial obtained by the methods disclosed herein.

As used herein, the singular forms "a", "an" and "the" mean to include the plural forms as well, unless the context clearly indicates otherwise.

As used herein, the terms "about" or "approximately" may be used interchangeably and when used in conjunction with a stated numerical value or range denotes somewhat more or somewhat less than the stated value or range, to within a range of ±10% of that stated.

As used herein, the term "biocompatible" means a composition or article that does not cause or causes tolerable or acceptable levels of toxic or injurious effects on biological systems.

As used herein, the term "biomaterial(s)" means a composition or article that is biocompatible. The biomaterial can include compositions or articles in different physical forms, such as a coating, fiber, film, foam, gel, graft, hydrogel, membrane, mesh, scaffold, sheet, sponge, or mesh and the like. These articles can include natural products, synthetic products, or combinations thereof. In particular aspects, biomaterials may be used in a medical treatment or diagnostic application(s).

As used herein, the term "carrier(s)" means any suitable substance which can deliver a keratin nanomaterial.

As used herein, the term "consisting essentially of" means unspecified components may be present if the characteristics of the claimed composition are thereby not materially affected.

As used herein, the term "keratin(s)" means the family of fibrous structural proteins or intermediate filaments. Each Type I keratin is co-expressed with a specific Type II keratin partner. Keratin proteins form filamentous polymers in a series of assembly steps beginning with dimerization of Type I and Type II monomers. Dimers assemble into tetramers and octamers and eventually into unit length filaments capable of annealing end-to-end into long filaments.

As used herein, the term "keratin nanomaterial(s)" means molecular complexes of Type I and Type II monomers, such as dimers of Type I and Type II monomers, the dimers having a length of 20-75 nm, a width of 1-5 nm, and a molecular weight in the range of 100-200 kDa, and/or tetramers of two such dimers, the tetramers having a length of 50-100 nm, a width of 5-10 nm, and a molecular weight in the range of 200-600 kDa.

As used herein, the term "purified" means keratin nanomaterials free from unwanted or inferior components. The term "purified" also covers keratin nanomaterials free from components from the source material from which it is obtained. The keratin nanomaterial may be "substantially pure," that is, free from other components from the source material in which it is produced, that is, for example, wool, feathers, hair fibers, and the like. In preferred embodiments, the keratin nanomaterials are at least 75% (w/w) pure, more preferably at least 80%, at least 85%, at least 90%, at least 95%, at least 96%, at least 97%, at least 98%, or at least 99% pure. In another preferred embodiment, the keratin nanomaterial is 100% pure.

As used herein the term "isolate(s)" and "isolated" means a material that is removed from its natural state and separated from other molecules naturally associated with it.

As used herein, the term "source material(s)" means starting materials, such as proteinaceous sources of keratin proteins from animal or human origin.

Keratin Nanomaterials

As described throughout, the keratin nanomaterials may be any keratin nanomaterial. In embodiments, the keratin nanomaterial may be derived from a natural source material, a synthetic source material, or combinations thereof. In particular aspects, the keratin nanomaterial may be produced using oxidative chemistry, reductive chemistry, recombinantly, or combinations thereof.

In particular embodiments, the source material is a proteinaceous keratin material. Non limiting examples of proteinaceous keratin materials suitable for obtaining keratin nanomaterials include, hair, wool, fur, skin, horns, hooves, beaks, feathers, and scales and the like from animal origins. In a particular aspect, the source material is human hair. In another aspect the source is end cut human hair fibers. In still another aspect, the human hair is blond human hair or colored hair that has been bleached using methods known in the art. In still yet another aspect, the human hair is free of melanin, or substantially free of melanin. In another particular aspect, the source material is feathers. In still another aspect, the feathers are white feathers. In yet another aspect, the feathers are free of melanin or substantially free of melanin. In still another particular aspect, the source material is wool. In still another aspect, the wool is white wool. In yet another aspect, the wool is free of melanin or substantially free of melanin. The source material can be combinations of one or more proteinaceous keratin materials, such as one or more of the materials listed above.

In embodiments provided herein, the keratin nanomaterials comprise one or more Type I and Type II monomer pairs (e.g., at least one Type I and Type II monomer pairs, at least two Type I and Type II monomer pairs, at least three Type I and Type II monomer pairs, at least four Type I and Type II monomer pairs, and so on).

In a particular aspect, the keratin nanomaterials comprise one or more dimers of Type I and Type II monomers, one or more tetramers of two dimers, or a combination thereof. In a particular aspect, the keratin nanomaterials comprise one or more dimers of Type I and Type II monomers. In a more particular aspect the keratin nanomaterials consist essentially of one or more dimers of Type I and Type II monomers. In an even more particular aspect, the keratin nanomaterials consist of one or more dimers of Type I and Type II monomers. In another aspect the keratin materials comprise one or more tetramers of two dimers of Type I and Type II monomers. In a more particular aspect, the keratin nanomaterials consist essentially of one or more tetramers of two dimers of Type I and Type II monomers. In an even more particular aspect, the keratin nanomaterials consist of one or more tetramers of two dimers of Type I and Type II monomers.

As shown in FIG. 1 and described herein, keratin nanomaterials are themselves not damaged and are devoid or nearly devoid of unwanted components such as associated (i.e., attached to, bound to, etc.) damaged keratin monomers or peptides and other contaminants. Removal of associated damaged keratin monomers and peptides is not accomplished by methods known in the art and must be performed using the methods described herein. Once these contaminants are removed, stable keratin nanomaterials are produced that are capable of significant self-assembly into biomaterials with desirable properties, including greater stability of the biomaterials so formed. In embodiments provided herein, the keratin nanomaterials range in purity between about 60% to about 100% pure (e.g., about 60% pure, 65% pure, 70% pure, 75% pure, 80% pure, 85% pure, 90% pure, 91% pure, 92% pure, 93% pure, 94% pure, 95% pure, 96% pure, 97% pure, 98% pure, 99% pure, up to about 100% pure).

Further, as provided herein the keratin nanomaterials comprise dimers and tetramers of different lengths and diameters. In one aspect, the dimers range between about 5 nm to about 75 nm in length (e.g., from about 5 nm long, 7.5 nm long, 10 nm long, 12.5 nm long, 15 nm long, 17.5 nm long, 20 nm long, 22.5 nm long, 25 nm long, 27.5 nm long, 30 nm long, 32.5 nm long, 35 nm long, 37.5 nm long, 40 nm long, 42.5 nm long, 45 nm long, 47.5 nm long, 50 nm long, 52.5 nm long, 55 nm long, 57.5 nm long, 60 nm long, 62.5 nm long, 65 nm long, 67.5 nm long, 70 nm long, 72.5 nm long, up to about 75 nm long) and range between about 0.5 nm to about 10 nm in diameter (e.g., from about 0.5 nm in diameter, 1 nm in diameter, 1.5 nm in diameter, 2 nm in diameter, 2.5 nm in diameter, 3 nm in diameter, 3.5 nm in diameter, 4 nm in diameter, 5 nm in diameter, 5.5 nm in diameter, 6 nm in diameter, 6.5 nm in diameter, 7 nm in diameter, 7.5 nm in diameter, 8 nm in diameter, 8.5 nm in diameter, 9 nm in diameter, 9.5 nm in diameter, up to about 10 nm in diameter). In a particular aspect, the dimers are about 50 nm long and about 2 nm in diameter.

In one aspect, the tetramers range between about 25 nm to about 200 nm in length (e.g., from about 25 nm long, 30 nm long, 35 nm long, 40 nm long, 45 nm long, 50 nm long, 55 nm long, 60 nm long, 65 nm long, 70 nm long, 75 nm long, 80 nm long, 85 nm long, 90 nm long, 95 nm long, 100 nm long, 105 nm long, 110 nm long, 115 nm long, 120 nm long, 125 nm long, 130 nm long, 135 nm long, 140 nm long, 145 nm long, 150 nm long, 155 nm long, 160 nm long, 165 nm long, 170 nm long, 175 nm long, 180 nm long, 185 nm long, 190 nm long, 195 nm long, up to about 200 nm long) and range between about 1 nm to about 20 nm in diameter (e.g., from about 1 nm in diameter, 1.5 nm in diameter, 2 nm in diameter, 2.5 nm in diameter, 3 nm in diameter, 3.5 nm in diameter, 4 nm in diameter, 4.5 nm in diameter, 5 nm in diameter, 5.5 nm in diameter, 6 nm in diameter, 6.5 nm in diameter, 7 nm in diameter, 7.5 nm in diameter, 8 nm in diameter, 8.5 nm in diameter, 9 nm in diameter, 9.5 nm in diameter, 10 nm in diameter, 11 nm in diameter, 11.5 nm in diameter, 12 nm in diameter, 12.5 nm in diameter, 13 nm in diameter, 13.5 nm in diameter, 14 nm in diameter, 14.5 nm in diameter 15 nm in diameter, 15.5 nm in diameter, 16 nm in diameter, 16.5 nm in diameter, 17 nm in diameter, 17.5 nm in diameter, 18 nm in diameter, 18.5 nm in diameter, 19 nm in diameter, 19.5 nm in diameter, up to about 20 nm in diameter). In another aspect, the tetramers associate in different staggered conformations and can be from approximately 50 to 100 nm long and approximately 5 to 10 nm in diameter.

Methods of Producing Keratin Nanomaterials

As provided throughout, the described keratin nanomaterials can be obtained according to the processes described herein. The method steps disclosed herein can be repeated as many times as necessary so long as keratin nanomaterials are produced (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, and so on).

As a primary step, the methods disclosed herein comprise obtaining a solution of soluble keratins. In a particular aspect, the solution is a solution of soluble trichocytic keratins, cytokeratins, and combinations thereof. In another particular aspect, the solution is a solution of soluble cytokeratins. In still another particular aspect, the solution is a solution of soluble trichocytic keratins.

Solutions of soluble trichocytic keratins can be obtained using known methods in the art. Such methods include, for example, cleaving disulfide bonds as described by Crewther et al. (see Crewther, 1965). In particular, disulfide bonds can be cleaved using oxidative or reductive disulfide bond cleavage.

The keratin nanomaterials can be obtained from any source material. In embodiments, the keratin nanomaterial may be derived from a natural source material, a synthetic source material, or a combination thereof. In particular embodiments, the source material is a proteinaceous keratin material. Non limiting examples of proteinaceous keratin materials suitable for obtaining kertain nanomaterials include, hair, wool, fur, skin, horns, hooves, beaks, feathers, and scales and the like from animal origins. In a particular aspect, the source material is human hair. In another aspect the source is end cut human hair fibers. In still another aspect, the human hair is blond human hair or colored hair that has been bleached using methods known in the art. In still yet another aspect, the human hair is free of melanin, or substantially free of melanin. In another particular aspect, the source material is feathers. In still another aspect, the feathers are white feathers. In yet another aspect, the feathers are free of melanin or substantially free of melanin. In still another particular aspect, the source material is wool. In still another aspect, the wool is white wool. In yet another aspect, the wool is free of melanin or substantially free of melanin. In embodiments, the keratin nanomaterials can also be obtained by conventional chemical synthesis techniques or by producing the keratin nanomaterials using recombinant techniques.

Once disulfide bonds are effectively cleaved, or at the same time as bond cleavage, keratins can be extracted from the tissue network and put into appropriate solutions. Preferred solutions are known in the art and include, for example, urea, thiourea, phosphates, diphosphates, sulfates, disulfates, cyanates, thiocyanates, carbonates, bicarbonates, transition metal hydroxides (e.g. sodium and potassium hydroxide), ammonium hydroxide, and tris(hydroxymethyl) aminomethane (Trizma® base). In particular aspects, the solutions have a concentration ranging from about 0.01 M to about 1.0 M (e.g., about 0.01 M, 0.05 M, 0.10 M, 0.15 M, 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M, 0.85 M, 0.90 M, 0.91 M, 0.92 M, 0.93 M, 0.94 M, 0.95 M, 0.96 M, 0.97 M, 0.98 M, 0.99 M, up to about 1.0 M). In a particular embodiment, the concentration of the solution is about 0.1 M.

In another aspect, the solution is Trizma® base. In a more particular aspect, the concentration of Trizma® base ranges from about 0.01 M to about 1.0 M (e.g., about 0.01 M, 0.05 M, 0.10 M, 0.15 M, 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M, 0.85 M, 0.90 M, 0.91 M, 0.92 M, 0.93 M, 0.94 M, 0.95 M, 0.96 M, 0.97 M, 0.98 M, 0.99 M, up to about 1.0 M). In still a more particular embodiment, the concentration of Trizma® base is about 0.1 M.

In some embodiments, crude solutions of extracted keratins may receive additional clarification to remove small particulate materials (e.g., pieces of cuticle) which can be accomplished by methods known in the art. Non-limiting examples include, filtering, gravity setting, decanting, centrifuging, hydrocyclone separation, etc. In a particular aspect, further clarification may be performed using centrifugation. In an aspect, the centrifugation speed is between about 2,500 rpm to about 10,000 rpm (e.g., about 2,500 rpm, 2,750 rpm, 3,000 rpm, 3,500 rpm, 3,570 rpm, 4,000 rpm, 4,250 rpm, 4,500 rpm, 4,750 rpm, 5,000 rpm, 5,250 rpm, 5,500 rpm, 5,750 rpm, 6,000 rpm, 6,250 rpm, 6,500 rpm, 6,750 rpm, 7,000 rpm, 7,250 rpm, 7,500 rpm, 7,750 rpm, 8,000 rpm, 8,250 rpm, 8,500 rpm, 8,750 rpm, 9,000 rpm, 9,250 rpm, 9,500 rpm, 9,750 rpm, up to about 10,000 rpm). In a more particular aspect, the centrifugation speed is high speed centrifugation (e.g. >5,000 rpm).

In some embodiments, the clarification step may be further followed by a filtration process. Non limiting examples of filtration include gravity filtration, vacuum filtration, membrane filtration, and the like. In a particular aspect, the method of filtration is membrane filtration. In a more particular aspect, the membrane used for membrane filtration has a pore size between about 1 μm to about 50 μm (e.g., 1 μm, 5 μm, 10 μm, 15 μm, 20 μm, 25 μm, 30 μm, 35 μm, 40 μm, 45 μm, up to about 50 μm). In still a more particular aspect, the filtration method includes filtration through membranes with pore sizes of less than 50 μm.

In other embodiments, following clarification, crude keratin extract solutions may optionally undergo purification processes to yield sub-fractions of keratins. In some embodiments, sub-fractionation further removes gross contaminations and yields a more appropriate keratin solution for obtaining keratin nanomaterials therefrom. Sub-fractionation methods are known in the art and include, for example, isoelectric precipitation, ultrafiltration, and various forms of chromatography (e.g., column chromatography, paper chromatography, thin-layer chromatography, displacement chromatography, gas chromatography, liquid chromatography, etc.). In a particular aspect, sub-fractionation is performed using isoelectric precipitation. In a more particular aspect, the method of isoelectric precipitation is acidification. More particularly, in certain embodiments, an aqueous acid is added to a solution of keratin such that the pH reaches less than 6 (e.g., pH 1, pH 1.5, pH 2, pH 2.5, pH 3, pH 3.5, pH 4, pH 4.5, pH 5, pH 5.5, up to pH 6) and the precipitation of an acid-insoluble fraction is achieved. In more particular aspects, the range of acidity is between about pH 4 to about pH 6. Non-limiting examples of acids suitable for acidification include hydrochloric, sulfuric and acetic acids. In particular aspects, the acid is hydrochloric acid. The acid insoluble and acid soluble sub-fractions can then be separated by methods known in the art. Non-limiting examples methods for separating acid soluble sub-fractions include, filtering, gravity setting, decanting, centrifuging, hydrocyclone separation, etc. In a particular aspect, further clarification may be performed using centrifugation. In an aspect, the centrifugation speed is between about 2,500 rpm to about 10,000 rpm (e.g., about 2,500 rpm, 2,750 rpm, 3,000 rpm, 3,500 rpm, 3,570 rpm, 4,000 rpm, 4,250 rpm, 4,500 rpm, 4,750 rpm, 5,000 rpm, 5,250 rpm, 5,500 rpm, 5,750 rpm, 6,000 rpm, 6,250 rpm, 6,500 rpm, 6,750 rpm, 7,000 rpm, 7,250 rpm, 7,500 rpm, 7,750 rpm, 8,000 rpm, 8,250 rpm, 8,500 rpm, 8,750 rpm, 9,000 rpm, 9,250 rpm, 9,500 rpm, 9,750 rpm, up to about 10,000 rpm). In a more particular aspect, the centrifugation speed is high speed centrifugation (e.g. >5,000 rpm).

In certain embodiments, further purification can be optionally performed to keratin sub-fraction solutions such as, for example, chromatography. Several types of chromatography can be employed to purify keratin solutions including size exclusion or gel filtration chromatography, affinity chromatography, isoelectric focusing, gel electrophoresis, ion exchange chromatography, and immunoaffinity chromatography. Chromatography techniques are well known in the art and are capable of separating compounds, including proteins, by the characteristics of molecular weight, chemical functionality, isoelectric point, charge, or interactions with specific antibodies, and can be used alone or in any combination to affect high degrees of separation and resulting purity. In a particular aspect, purification is performed using ion exchange (IEx) chromatography. IEx chromatography is particularly suited to protein separation owning to the amphiphilic nature of proteins in general and keratins in particular. Depending on the starting pH of the solution and the desired fraction slated for retention, either cationic or anionic IEx (CIEx or AIEx, respectively) techniques can be used. For example, at a pH of 7 and above, both acid soluble and insoluble fractions are soluble and will display different resin binding characteristics depending on their isoelectric points. Without being bound to any specific theory, keratin sub-fraction solutions can be titrated to a target pH and passed through either CIEx or AIEx resin. Those skilled in the art will recognize that the molecules contained in the keratin sub-fractions will bind or not bind to the resin depending on their net charge at the target pH. Consequently, separation between further sub-fractions can be achieved by separately collecting the solution that passes through the resin, followed by a solution intended to remove compounds bound to the resin (e.g., sodium chloride or other buffer solutions). The fraction(s) containing keratin nanomaterials can be identified using analytical techniques known in the art such as, for example, gel electrophoresis, gel filtration chromatography, or size exclusion chromatography.

In other embodiments, ultrafiltration can be utilized for gross fractionation of crude keratin solutions, alone or in combination with the aforementioned methods. Ultrafiltration can be used to separate crude keratin solutions or keratin sub-fraction solutions with different molecular size characteristics. Without being bound to any specific theory of keratin behavior, the previously described acid insoluble sub-fraction is thought to be of relatively higher molecular weight than the acid soluble sub-fraction. Those of skill in the art will recognize how methods such as ultrafiltration can be applied to affect separation between proteins based on their molecular size and the selection of appropriate ultrafiltration conditions.

In a particular embodiment, the ultrafiltration membrane has a nominal low molecular weight cutoff (NLMWCO) in the range between about 10 kDa to about 300 kDa (e.g., about 10 kDa, 20 kDa, 30 kDa, 40 kDa, 50 kDa, 60 kDa, 70 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa up to about 300 kDa). In a particular aspect, the method for isolation of the higher molecular weight fraction of soluble keratins is ultrafiltration using a membrane with a NLMWCO of about 30 kDa. In still another particular aspect, the method for isolation of the higher molecular weight fraction of soluble keratins is ultrafiltration using a membrane with a NLMWCO of approximately 100 kDa.

It will be appreciated by those of ordinary skill in the art that the keratins that permeate the ultrafiltration membrane can also be collected such that molecules below a certain nominal molecular weight can also be isolated. Several ultrafiltration steps can be used in sequence, employing different NLMWCO membranes to isolate multiple molecular weight fractions of keratin. These steps can be employed either before or after other separation techniques as previously described, in many different combinations, to affect a multitude of separation and purification strategies.

Following the initial purification, keratin nanomaterials are further purified and produced (i.e., isolated) from the keratin solution(s). Keratin nanomaterials are produced by treating keratin solutions with a buffer. Non-limiting examples of buffers suitable for treating keratin solutions include monobasic and/or dibasic phosphates (e.g., sodium phosphate, sodium dihydrogen phosphate, disodium hydrogen phosphate, potassium phosphate, potassium dihydrogen phosphate and dipotassium hydrogen phosphate, etc.), borates (e.g., sodium borate, potassium borate, etc.) citrates (e.g., sodium citrate, disodium citrate, etc.), acetates (e.g., sodium acetate, potassium acetate, etc.) carbonates (e.g., sodium carbonate, sodium hydrogen carbonate, etc.), and the like. In a particular aspect, the buffers are monobasic phosphate buffers, dibasic phosphate buffers, or combinations thereof. In still a more particular aspect, the buffer is sodium phosphate buffer, potassium phosphate buffer, or a combination thereof.

The concentration of the buffer used for treating the keratin solution can range between about 1 mM to about 200 mM (e.g., 1 mM, 5 mM, 10 mM 15 mM, 20 mM, 25 mM 30 mM, 35 mM, 40 mM, 45 mM, 50 mM, 55 mM, 60 mM, 65 mM, 70 mM, 75 mM, 80 mM, 85 mM, 90 mM, 100 mM, 105 mM, 110 mM 115 mM, 120 mM, 125 mM 130 mM, 135 mM, 140 mM, 145 mM, 150 mM, 155 mM, 160 mM, 165 mM, 170 mM, 175 mM, 180 mM, 185 mM, 190 mM, up to about 200 mM). In a particular embodiment, the concentration of buffer is in the range between about 1 mM to 100 mM. In still a more particular embodiment, the concentration of buffer is in the range between about 5 mM to about 50 mM. The pH of the buffer solution will also affect purification. In certain aspects, the pH for the buffer solutions provided herein is in the range between about pH 7 to about pH 12 (e.g., about pH 7, pH 7.5, pH8, pH 8.5, pH 9, pH 9.5, pH 10, pH 10.5, pH 11, pH 115, up to about pH 12). In a more particular aspect, the pH range is between about pH 7 to about pH 10. In still a more particular aspect, the pH range is between about pH 7.4 to about pH 10.

The buffer solutions used herein may also contain other solutes such as, for example, chloride salts. Non-limiting examples of chloride salts include, for example, sodium or potassium chloride. In a particular embodiment, sodium chloride is used with sodium phosphate buffers, potassium chloride is used with potassium phosphate buffers is potassium chloride, or a combination thereof is used. In a particular aspect, the concentration of chloride salt is in the range of about 1 mM to about 1 M (e.g., about 1 mM, 50 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, up to about 1M). In a more particular aspect, the concentration of chloride salt is between about 50 mM to about 200 mM.

Without being bound to any particular theory, the use of phosphate buffers in the disclosed concentration range serves to destabilize the binding of associated (i.e., bound to) damaged proteins and peptides to the core keratin nanomaterial while enhancing the stability of the keratin nanomaterial itself. In some embodiments, the buffer salts are added to the keratin solution and allowed to stand while molecular re-arrangement of the keratin nanomaterials occurs. In an embodiment, the keratin solutions are allowed to stand for a time period between about 30 seconds to about 30 days. In still other embodiments, the salts are added during the process of ultrafiltration by utilizing addition of make-up buffer. In a particular embodiment, the buffer is phosphate buffer and the concentration of phosphate buffer is 1 mM to 100 mM. In a particular aspect, the concentration of phosphate buffer is 5 mM to 50 mM. In further aspects, the pH range for phosphate buffer solutions is pH 7 to pH 12. In a more particular aspect, the pH range for phosphate buffer solutions is pH 7 to pH 10. In still yet a more particular aspect, the pH for phosphate buffer solutions is pH 7.4 to pH 10. In an even more particular embodiment, the phosphate buffer solution includes one or more chloride salts. In a particular aspect, the chloride salt for use with sodium phosphate buffers is sodium chloride, and the chloride salt for use with potassium phosphate buffers is potassium chloride. In particular aspects, the concentration of chloride salt is 10 mM to 1 M, such as from 50 mM to 200 mM.

Once these molecular re-arrangements occur (or as they are occurring), ultrafiltration can be performed again to remove the now disassociated damaged keratin and peptide molecules. In a particular embodiment, tangential flow ultrafiltration is performed with a NLMWCO membrane between about 10 kDa to about 300 kDa (e.g., about 10 kDa, 20 kDa, 30 kDa, 40 kDa, 50 kDa, 60 kDa, 70 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa up to about 300 kDa). In a particular aspect, tangential flow ultrafiltration is performed with a NLMWCO membrane of approximately 30 kDa. In still yet another particular aspect, tangential flow ultrafiltration is performed with a NLMWCO membrane of approximately 100 kDa. Those skilled in the art will recognize that keratin nanomaterials ranging in molecular size from about 50 nm to about 100 nm can be further separated utilizing ultrafiltration membranes with different NLMWCO values.

Once isolated, the keratin nanomaterials can be further purified, if desired, by removing buffer salts using ultrafiltration, acid precipitation, or other methods as described previously. In particular embodiments, the method for removing the buffer salts is ultrafiltration, more particularly, ultrafiltration against purified water. In some embodiments, it may be advantageous to repeat cycles of buffer ultrafiltration and purified water ultrafiltration, in various combinations, to affect more desirable purification of keratin nanomaterials. In addition, it may be beneficial to end ultrafiltration with a specific buffer so that the sample is osmotically balanced.

Once purification is complete, keratin nanomaterials can be isolated by methods known in the art. These methods include concentration of the solution followed by solidification. Solid keratin nanomaterials can be obtained from solutions using freeze drying, critical point drying, falling film evaporation, spray drying, or the like. In particular aspects, keratin nanomaterials are isolated using methods such as critical point drying and freeze drying, and in more particular aspects, freeze drying. Those skilled in the art will recognize that several parameters of freeze drying such as freezing temperature, freezing rate, drying temperature and drying rate will affect the resulting solid keratin nanomaterials.

A preferred method of freeze drying is to use controlled freezing and drying rates. In a particular aspect, the freezing rate ranges from about 0.01° C. to 10° C. per minute (e.g., about 0.01° C., 0.05° C., 0.10° C., 0.15° C., 0.20° C., 0.25° C., 0.30° C., 0.35° C., 0.40° C. 0.45° C. 0.50° C. 0.55° C. 0.60° C. 0.65° C. 0.70° C. 0.75° C. 0.80° C. 0.85° C. 0.90° C. 0.91° C. 0.92° C. 0.93° C. 0.94° C. 0.95° C. 0.96° C. 0.97° C. 0.98° C. 0.99° C. 1.0° C., 1.5° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., up to 10° C. per minute). In a particular aspect, the freezing rate is nearly instantaneous, such as can be achieved by quenching the keratin nanomaterial solution in liquid nitrogen, isopropanol/dry ice, or the like. In a more particular aspect, the freezing rate ranges from about 0.1° C. to about 1° C. per minute (e.g., about 0.10° C., 0.15° C., 0.20° C., 0.25° C., 0.30° C. 0.35° C. 0.40° C. 0.45° C. 0.50° C. 0.55° C., 0.60° C., 0.65° C., 0.70° C., 0.75° C., 0.80° C., 0.85° C., 0.90° C., 0.91° C., 0.92° C., 0.93° C., 0.94° C., 0.95° C., 0.96° C., 0.97° C., 0.98° C., 0.99° C., up to about 1.0° C. per minute).

In particular embodiments, the preferred drying rate is that which is achieved when the sample is under high vacuum and below the freezing point of water. In a particular embodiment the vacuum is in the range between about 1 millitorr to about 100 millitorr (e.g., about 1 millitorr, 5 millitorr, 10 millitorr, 15 millitorr, 20 millitorr, 25 millitorr, 30 millitorr, 35 millitorr, 40 millitorr, 45 millitorr, 50 millitorr, 55 millitorr, 60 millitorr, 65 millitorr, 70 millitorr, 75 millitorr, 80 millitorr, 85 millitorr, 90 millitorr, 95 millitorr, up to about 100 millitorr). In a more particular embodiment the vacuum is below 100 millitorr. In an even more particular aspect, the vacuum is below 80 millitorr.

For freeze drying, the sample temperature or the temperature that the sample is exposed to can be in the range between about −200° C. to about 0° C. (e.g., about −20° C., −19° C., −18° C., −17° C., −16° C., −15° C., −14° C., −13° C., −12° C., −11° C., −12° C., −10° C., −9° C., −8° C., −7° C., −6° C., −5° C., −4° C., −3° C., −2° C., −1° C., up to about 0° C.). In a particular aspect, the sample temperature or the temperature that the sample is exposed to is below 0° C. In a more particular aspect, the sample temperature or the temperature the sample is exposed to below −4° C. Those skilled in the art will recognize that residual water can be removed from the sample during the freeze drying process by affecting the sublimation process with different combinations of sample temperatures and vacuum, and that those most efficient and effective are ones in which sublimation rate is optimized. A preferred sublimation rate is one in which the sample is not allowed to thaw so that water is removed only by sublimation and not by evaporation.

Compositions

The compositions disclosed comprise at least one keratin nanomaterial described herein. In other embodiments, the compositions may optionally comprise a carrier. The compositions can be used to further produce keratin biomaterials.

In certain embodiments, the compositions described herein may be in the form of a gel, a foam, a solid (such as a powder, granule, particle, etc.), a slurry, or a liquid. In a particular aspect, the composition is in the form of a gel. In another particular aspect, the composition is in the form of a foam. In still another particular aspect, the composition is in the form of a solid (e.g., a powder, granule, particle, etc.). In yet another particular aspect, the composition is in the form of a slurry. In still yet another particular aspect, the composition is in the form of a liquid.

Carrier(s):

Compositions comprising carriers will have the correct values (and range of values) for rheological measurements (e.g., viscosity, yield value, storage modulus, and loss modulus). Non-limiting examples of carriers described herein include liquids, gels, foams, slurries, or solids (including wettable powders or dry powders).

The selection of the carrier material will depend on the intended application. In a particular embodiment, the carrier is a liquid. In an aspect, the liquid may be an aqueous or non-aqueous liquid carrier. Non-limiting examples of liquids useful as carriers for the compositions disclosed herein include water, an aqueous solution (e.g., sugar water), a non-aqueous liquid, or a non-aqueous solution. In a particular aspect, the carrier is water. In another aspect the carrier is an aqueous solution. In yet another aspect, the carrier is a non-aqueous liquid.

In a particular aspect, the carrier is a non-aqueous liquid (e.g., an oil, etc.). The non-aqueous liquid may be a biodegradable non-aqueous liquid. The non-aqueous liquid may be a "Low Vapor Pressure Volatile Organic Compounds (LVP-VOC)," which is a chemical "compound" or "mixture of compounds" containing (1) a vapor pressure less than 0.1 mm Hg at 20° C., (2) composed of chemical compounds with more than 12 carbon atoms and/or (3) a boiling point greater than 216° C. See the definition of LVP-VOC provided by the California Air Resources Board (CARB). The non-aqueous liquid may be a biodegradable LVP-VOC non-aqueous liquid.

Non-limiting examples of non-aqueous liquids suitable as a carrier for the compositions described herein include silicone oils, paraffinic/paraffin oils, mineral oils, hexylene glycol, glycerol, linoleic acid, oleic acid, and any combination thereof.

In another embodiment, the carrier is a slurry. Non-limiting examples of liquids appropriate for a slurry can include water, aqueous solutions, non-aqueous liquids, or non-aqueous solutions. In an aspect, the slurry may comprise a sticking agent, a liquid, or a combination thereof. Non-limiting examples of sticking agents include alginate, mineral oil, syrup, gum arabic, honey, methyl cellulose, milk, wallpaper paste, and combinations thereof.

In another embodiment, the carrier is a solid. In an aspect, the solid is a powder. In one aspect the powder is a wettable powder. In another aspect, the powder is a dry powder. In still another aspect, the solid is a granule. Non-limiting examples of solids useful as carriers for the compositions disclosed herein include peat, wheat, wheat chaff, ground wheat straw, bran, vermiculite, cellulose, starch, soil (pasteurized or unpasteurized), gypsum, talc, clays (e.g., kaolin, bentonite, montmorillonite), and silica gels.

Keratin Biomaterials

Keratin nanomaterials can be further processed or synthesized, isolated, purified, or otherwise prepared by other techniques using methods known to those skilled in the art. Keratin nanomaterials can be added to liquid solutions, solids (e.g., powders, wettable powders, etc.), slurries, semi-solids, pastes, emulsifications, etc.

In a particular embodiment, dried keratin nanomaterials can be further processed by grinding (e.g., comminuting, milling, etc.) the keratin nanomaterials into powder. Milling devices are known in the art. In a preferred embodiment, the keratin nanomaterials are ground using a pharmaceutical mill that employs a cone and screen technology. More particularly are pharmaceutical mills having cone and screen mills that reduce static charge.

Keratin biomaterials can be produced from keratin nanomaterials, compositions comprising keratin nanomaterials, or combinations thereof. In a particular embodiment, using processed keratin nanomaterials (e.g., a powdered keratin nanomaterial) one or more biomaterials comprising keratin nanomaterials can be formed according to methods known to those skilled in the art. Non-limiting examples of biomaterials comprising keratin nanomaterials include films, foams, fibers, coatings, gels, hydrogels, scaffolds, sponges, particles, etc. In more particular embodiments, biomaterials comprising the keratin nanomaterials provided herein further include putties, adhesives, dressings (such as medical dressings or components of medical dressings), bandages or components of bandages, drug delivery devices, cell delivery devices, etc.

In yet more particular embodiments, biomaterials comprising the keratin nanomaterials provided herein may further include coatings on medical devices, hydrogel particles containing cells including therapeutic cells such as stem cells, solid particles containing therapeutic agents such as drugs or biologic molecules such as growth factors, particles not containing cells or other compounds, sponges and/or foams used as tissue engineering scaffolds, fluids such as resuscitation fluids and/or fluids for organ preservation, dressings such as wound dressings, soft tissue bulking agents such as dermal fillers, and additives in cosmetic and personal care products.

EXAMPLES

The following examples are provided for illustrative purposes and are not intended to limit the scope of the invention as claimed herein. Any variations in the exemplified examples which occur to the skilled artisan are intended to fall within the scope of the present disclosure.

Example 1

Preparation of Oxidized Keratin Nanomaterials

A sample of human Chinese hair was obtained from a commercial vendor and used as received. 100 g of hair fibers was placed into 2 L of 2 wt/vol percent peracetic acid and shaken at 150 rpm for 8 hours at 37° C. The oxidized hair was recovered by sieve and extracted with 4 L of 100 mM tris base by shaking at 150 rpm for 15 hours at 37° C. The hair was recovered by sieve, the extract solution was retained, and the hair fibers further extracted with 4 L of purified water by shaking at 150 rpm for 2 hours at 37° C. The hair was recovered by sieve and discarded, and the extract solution retained. Both extract solutions were combined to form a solution of crude keratin extract, which was clarified of particulate matter by centrifugation through a solids separator running at 40,000 rpm followed by filtration through a membrane with 20-25 µm average pore size. Keratin nanomaterials were obtained from this crude solution by ultrafiltration using a 100 kDa NLMWCO polysulfone, spiral wound filter cartridge. The buffer used consisted of 5 mM disodium phosphate plus 150 mM sodium chloride at pH 7.5 and the ultrafiltration was conducted for 5 volume washes. A second phase of ultrafiltration was conducted with 5 volume washes of purified water. The purified keratin nanomaterial solution was concentrated, titrated to pH 7.4, frozen, and freeze dried to produce a keratin nanomaterial powder. The powder was reconstituted at 10, 8, and 5 weight percent with purified water. All three samples formed viscous, self-supporting hydrogels that did not flow under their own weight.

The sample of keratin nanomaterial was analyzed by size exclusion chromatography (SEC) to determine its molecular weight profile before and after buffer ultrafiltration. Samples were analyzed on a Dionex SEC chromatography system containing an Ultimate 3000 quaternary analytical pump, Rheodyne manual injector with a 20 microliter loop, and Ultimate 3000 UV/Vis detector. The mobile phase, flowing at mL/min, was 15 mM dibasic sodium phosphate/150 mM sodium chloride at pH 7.5. Detection was at 280 nm and data collection was performed using a laptop computer running Chromeleon v6.8 chromatography software. Samples were prepared as 0.2 mg/mL solutions in mobile phase buffer.

Figure 2A:
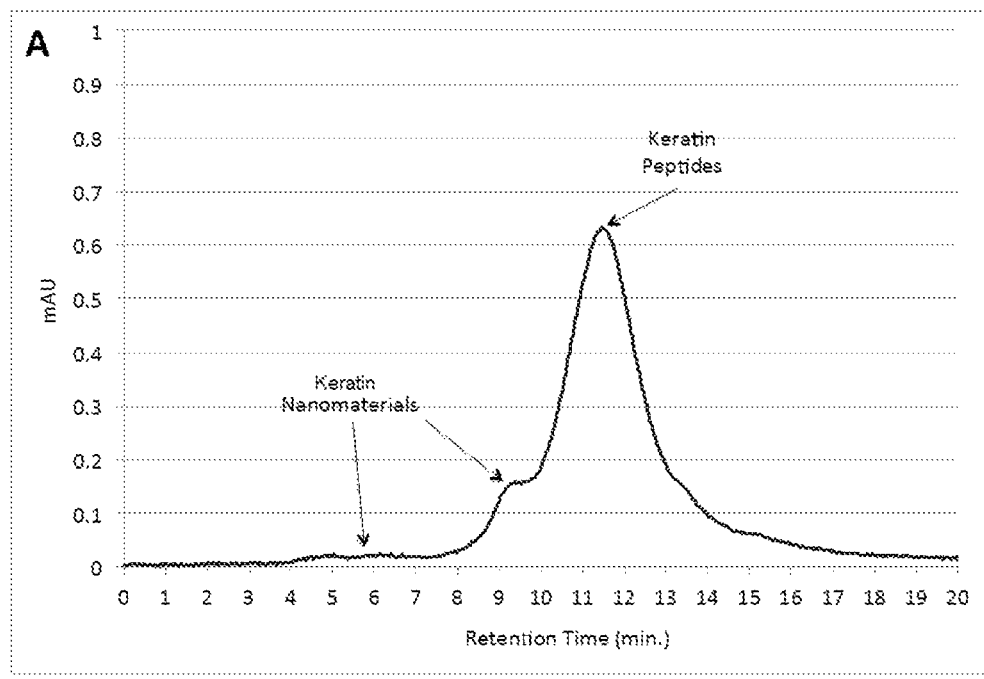
FIG. 2A is a graphical representation showing the presence of keratin nanomaterials and keratin peptides prior to buffer ultrafiltration.
Figure 2B:
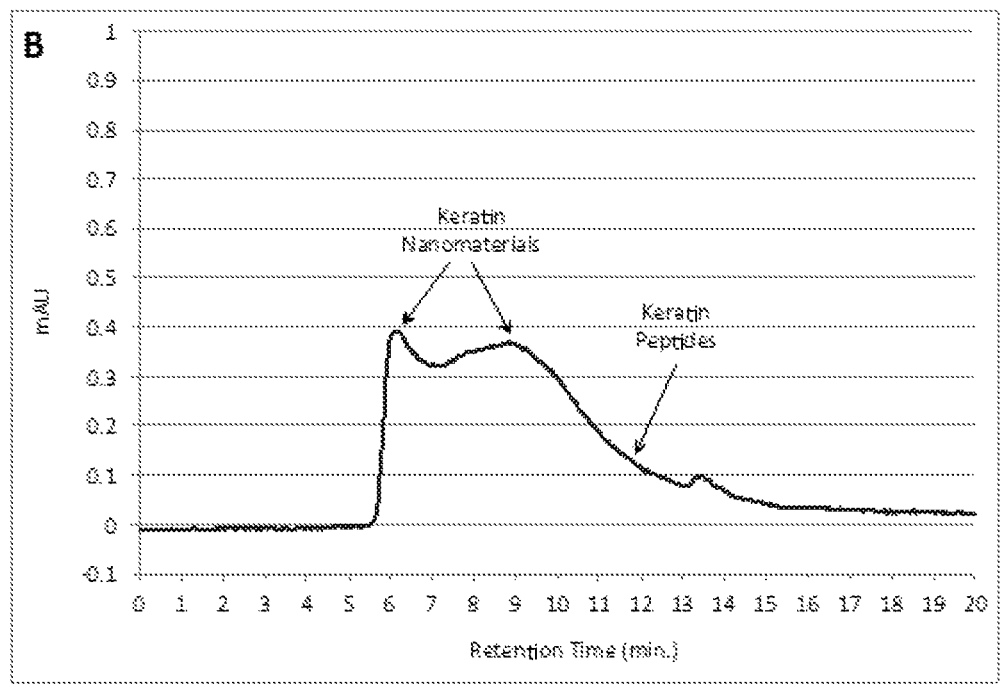
FIG. 2B is a graphical representation showing the presence of keratin nanomaterials after buffer ultrafiltration.

Results show predominantly keratin peptides and other low molecular weight compounds prior to buffer ultrafiltration (FIG. 2A). After buffer ultrafiltration, the presence of large amounts of keratin nanomaterial is clear (FIG. 2B).

Example 2

Preparation of Oxidized Keratin Nanomaterials

A sample of human Chinese hair was obtained from a commercial vendor and used as received. 200 g of hair fibers was placed into 4 L of 2 wt/vol percent peracetic acid and shaken at 125 rpm for 8 hours at 37° C. The oxidized hair was recovered by sieve and extracted with 8 L of 100 mM tris base by shaking at 125 rpm for 14 hours at 37° C. The hair was recovered by sieve, the extract solution was retained, and the hair fibers further extracted with 8 L of purified water by shaking at 125 rpm for 2 hours at 37° C. The hair was recovered by sieve and discarded, and the extract solution retained. Both extract solutions were combined to form a solution of crude keratin extract, which was clarified of particulate matter by centrifugation through a solids separator running at 43,000 rpm followed by filtration through a membrane with 20-25 µm average pore size. Keratin nanomaterials were obtained from this crude solution by ultrafiltration using a 100 kDa NLMWCO polysulfone, spiral wound filter cartridge. The buffer used consisted of 10 mM disodium phosphate plus 100 mM sodium chloride at approximately pH 9.1 and the ultrafiltration was conducted for 12 volume washes. A second phase of ultrafiltration was conducted with 4 volume washes of purified water. The purified keratin nanomaterial solution was concentrated, titrated to pH 7.4, frozen, and freeze dried to produce a keratin nanomaterial powder. The sample of keratin nanomaterials was analyzed by size exclusion chromatography (SEC) to determine its molecular weight profile before and after buffer ultrafiltration.

Samples were analyzed on a Dionex SEC chromatography system containing an Ultimate 3000 quaternary analytical pump, Rheodyne manual injector with a 20 microliter loop, and Ultimate 3000 UV/Vis detector. The mobile phase, flowing at 1 mL/min, was 10 mM dibasic sodium phosphate/100 mM sodium chloride at pH 7.5. Detection was at 280 nm and data collection was performed using a laptop computer running Chromeleon v6.8 chromatography software. Samples of keratin nanomaterial and conventional keratose were prepared as 0.2 mg/mL solutions in mobile phase buffer and analyzed for molecular weight.

Figure 3A:
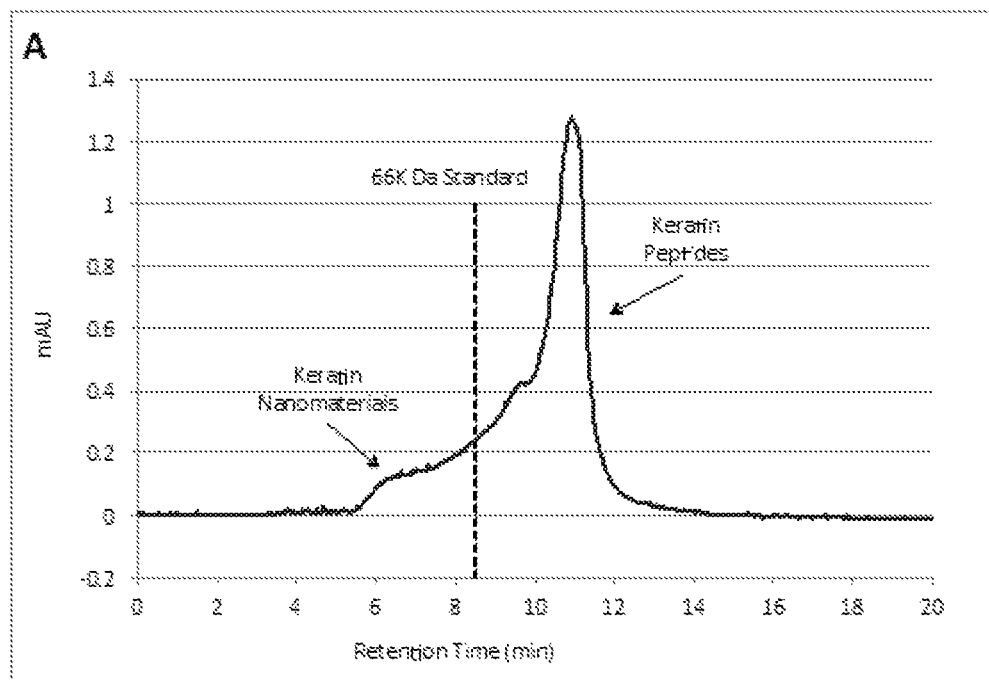
FIG. 3A is a graphical representation showing the presence of keratin nanomaterials and keratin peptides prior to buffer ultrafiltration.
Figure 3B:
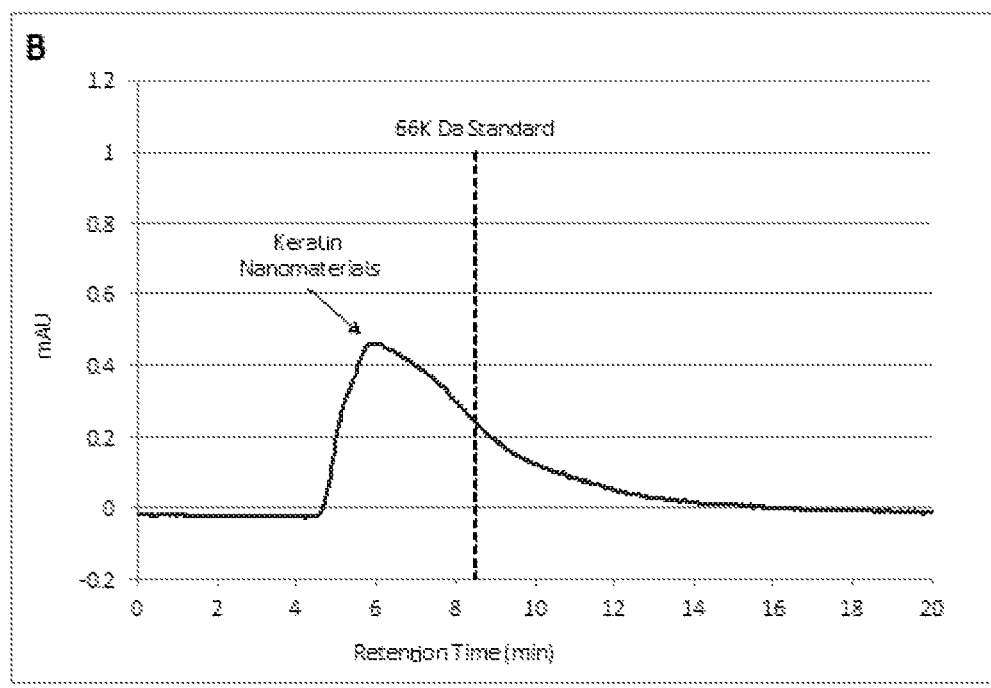
FIG. 3B is a graphical representation showing the presence of keratin nanomaterials after buffer ultrafiltration.

Results show predominantly keratin peptides and other low molecular weight compounds using conventional water ultrafiltration (FIG. 3A). Using buffer ultrafiltration, the presence of large amounts of keratin nanomaterial is clear (FIG. 3B).

Example 3

Preparation of Reduced Keratin Nanomaterials

A sample of human Chinese hair was obtained from a commercial vendor and used as received. Keratin extraction was accomplished through a multistep reductive process described as follows: 100 grams of hair was placed into a 2 L solution of 0.5 M thioglycolic acid (TGA) adjusted to a pH of 10.5 and shaken at 150 rpm for 15 hours at 37° C. The hair was recovered by sieve and the extraction solution retained. The hair fibers were then placed in a solution of 4 L 100 mM tris and shaken at 150 rpm for 2 hours at 37° C. The resulting extraction solution was retained and the hair was placed in 4 L of purified water and shaken at 150 rpm for 2 hours at 37° C. Hair was recovered by sieve and placed in a freshly prepared 1 L solution of 0.5 M TGA adjusted to a pH of 10.5 and shaken at 150 rpm for 15 hours at 37° C. The hair was recovered by sieve and the extraction solution retained. The hair was then placed in a 2 L solution of 100 mM tris and shaken at 150 rpm for 2 hours at 37° C. The resulting extraction solution was retained and the hair was then placed in 2 L of purified water and shaken at 150 rpm for 2 hours at 37° C. The hair was recovered by sieve and discarded. The extraction solution was retained and pooled with extraction solutions obtained in previous steps to form a solution of crude keratin extract. The extract was clarified of particulate matter by centrifugation through a solids separator running at 30,000 rpm followed by filtration through a membrane with a 20-25 µm average pore size. Keratin nanomaterials were obtained from this clarified crude keratin extract by ultrafiltration using a 100 kDa NLMWCO polysulfone, spiral wound filter cartridge. Ultrafiltration was conducted with 10 volume washes against a buffer consisting of 5 mM disodium phosphate and 150 mM sodium chloride at pH 9.1, followed by 3 volume washes against purified water. The purified keratin nanomaterial solution was concentrated, titrated to pH 8.5, frozen and freeze dried to produce a keratin nanomaterial powder.

Samples collected before and after ultrafiltration were analyzed using SEC to determine the relative molecular weight profile of the keratin nanomaterials. Samples were analyzed on a Dionex manual injector with a 20 microliter loop and Ultimate 3000 UV/Vis detector set at 280 nm. Data collection was performed using the Chromeleon v6.8 chromatography software.

Figure 4A:
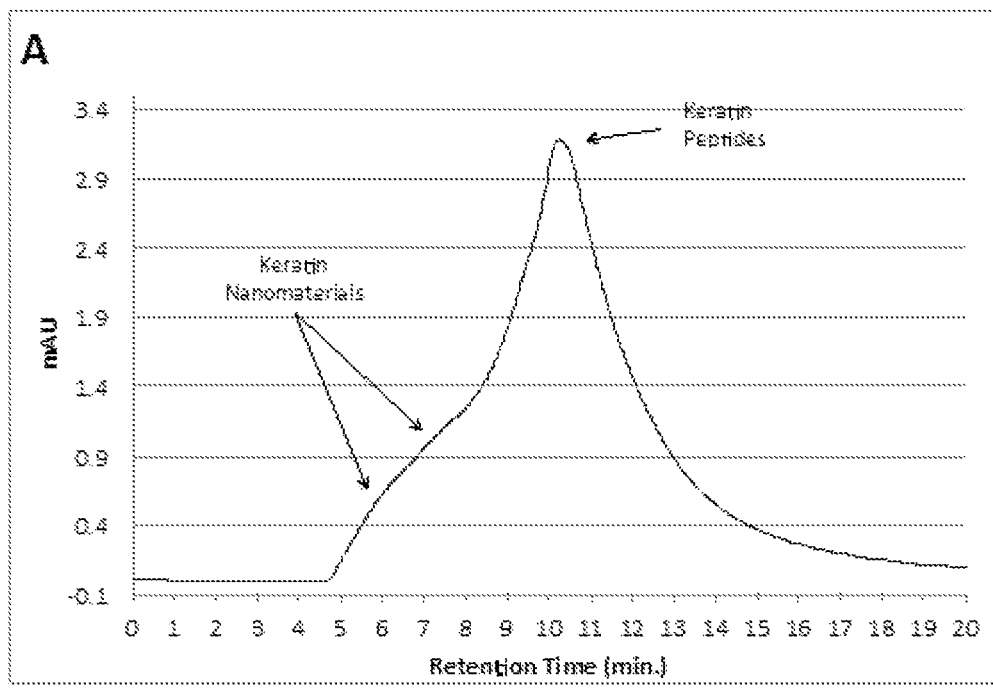
FIG. 4A is a graphical representation showing the presence of keratin nanomaterials and keratin peptides prior to buffer ultrafiltration.
Figure 4B:
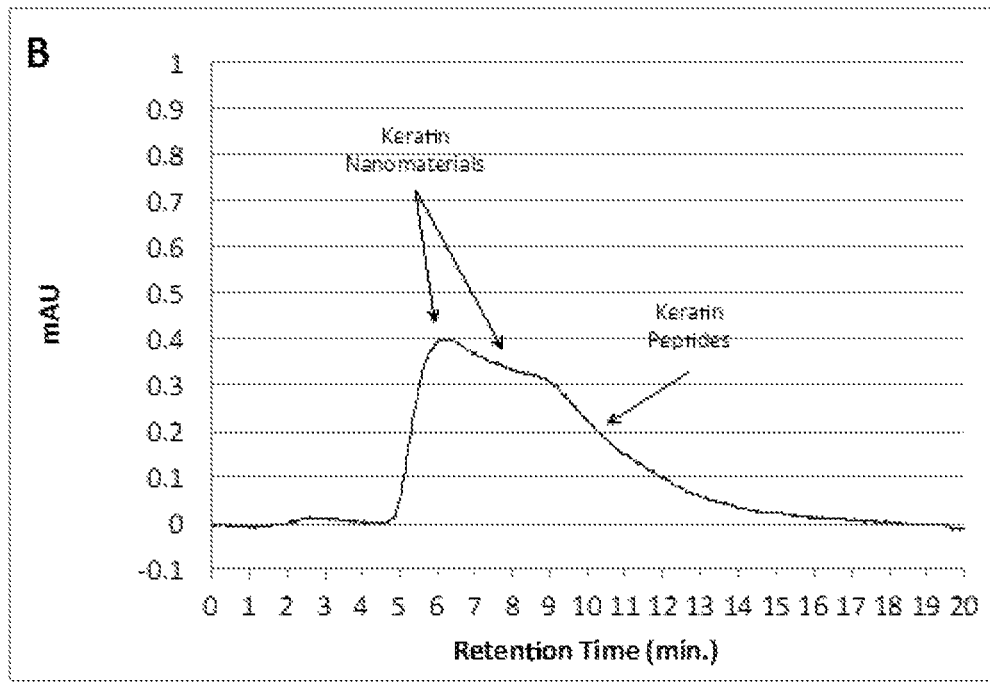
FIG. 4B is a graphical representation showing the presence of keratin nanomaterials after buffer ultrafiltration.

Resulting chromatograms demonstrate the presence of predominantly keratin peptides and other low molecular weight compounds in the keratin extract prior to ultrafiltration (FIG. 4A), whereas samples collected after ultrafiltration (FIG. 4B) clearly show the presence of keratin nanomaterials.

Example 4

Size Exclusion Chromatography of Keratin Samples

A sample of human Chinese hair was obtained from a commercial vendor and used as received. Keratin extraction was accomplished through a multistep reductive process described as follows: 50 grams of hair was placed into a 1 L solution of 0.5 M TGA adjusted to a pH of 10.5 and shaken at 150 rpm for 15 hours at 37° C. Following the incubation, the hair was recovered by sieve and the extraction solution retained. The hair fibers were then placed in a solution of 2 L 100 mM Tris and shaken at 150 rpm for 2 hours at 37° C. The resulting extraction solution was retained and the hair was placed in a 2 L solution of purified water and shaken at 150 rpm for 2 hours at 37° C. Hair was recovered by sieve and placed in a freshly prepared 0.5 L solution of 0.5 M TGA adjusted to a pH of 10.5 and shaken at 150 rpm for 15 hours at 37° C. The hair was recovered by sieve and the extraction solution retained. The hair was then placed in a 1 L solution of 100 mM Tris and shaken at 150 rpm for 2 hours at 37° C. The resulting extraction solution was retained and the hair was then placed in a 1 L solution of purified water and shaken at 150 rpm for 2 hours at 37° C. The hair was recovered by sieve and discarded. The extraction solution was retained and pooled with extraction solutions obtained in previous steps to form a solution of crude keratin extract. The extract was clarified of particulate matter by centrifugation through a solids separator running at 30,000 rpm followed by filtration through a membrane with a 20-25 µm average pore size. Keratin nanomaterials were obtained from this clarified crude keratin extract by ultrafiltration using a 100 kDa NLMWCO polysulfone, spiral wound filter cartridge. Ultrafiltration was conducted with 8 volume washes against a buffer consisting of 5 mM disodium phosphate and 150 mM sodium chloride at pH 9.1, followed by 3 volume washes against purified water. The purified keratin nanomaterial solution was concentrated, titrated to pH 8.5, frozen and freeze dried to produce a keratin nanomaterial powder.

Samples from both the buffer ultrafiltration and a replicate extraction process with conventional water ultrafiltration were analyzed using SEC to assess the presence of purified keratin nanomaterials. Samples were analyzed on a Dionex manual injector with a 20-microliter loop and Ultimate 3000 UV/Vis detector set at 280 nm. Data collection was performed using the Chromeleon v6.8 chromatography software.

Figure 5A:
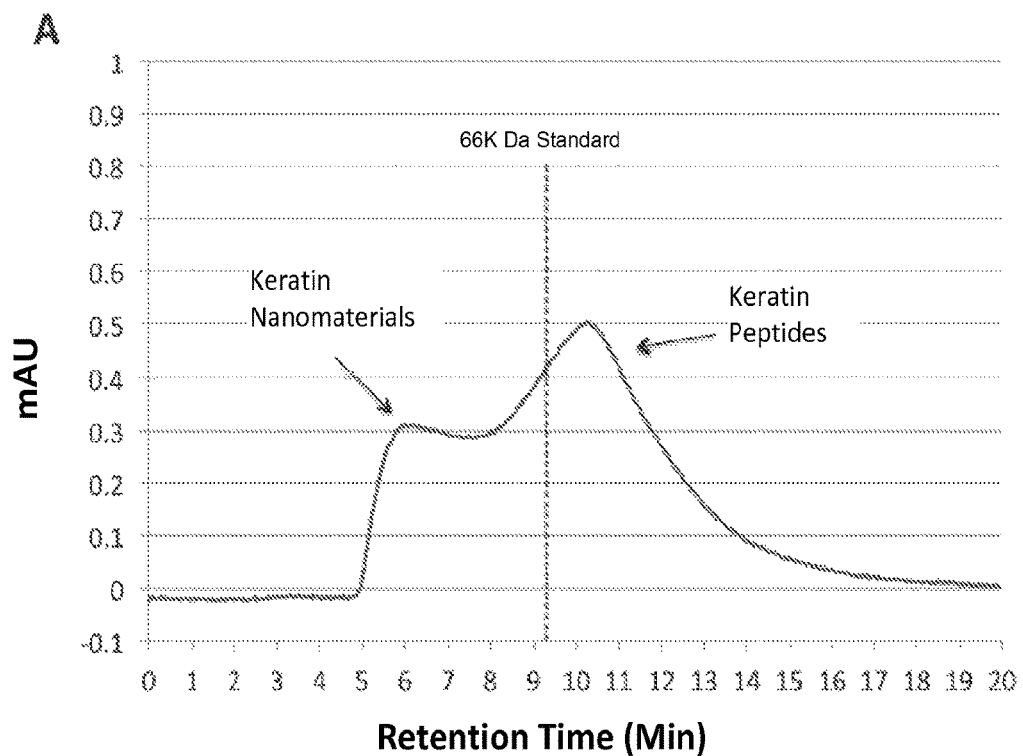
FIG. 5A is a graphical representation showing the presence of keratin nanomaterials and keratin peptides prior to buffer ultrafiltration.
Figure 5B:
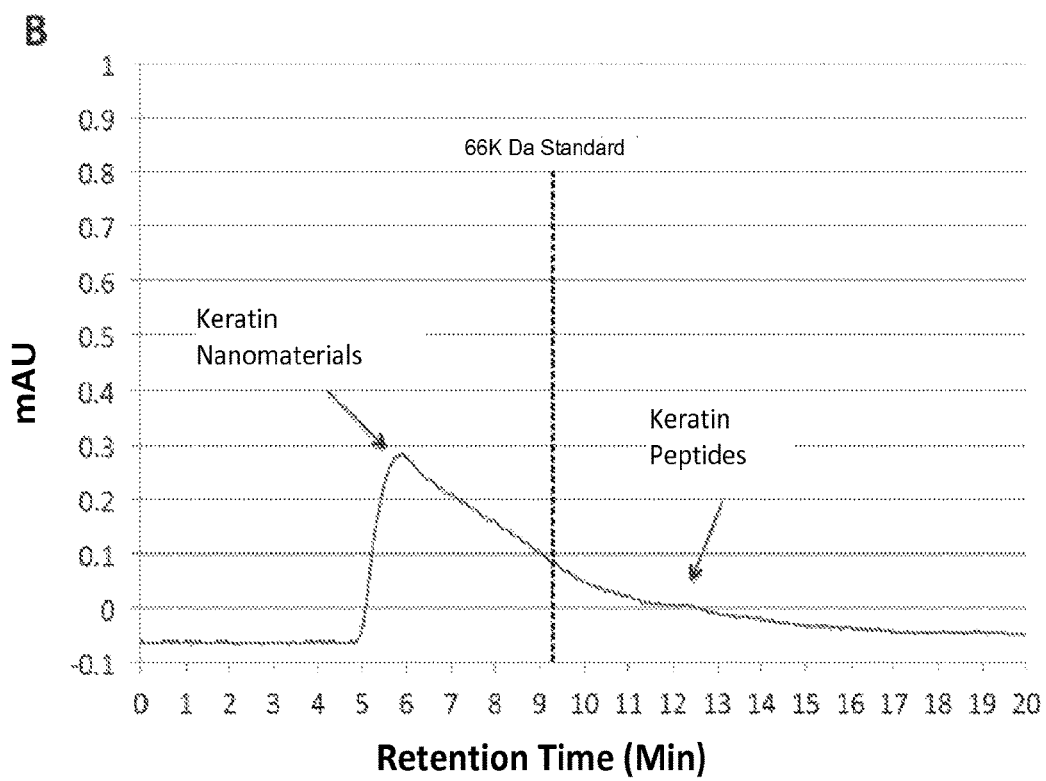
FIG. 5B is a graphical representation showing the presence of keratin nanomaterials after buffer ultrafiltration.

SEC chromatograms demonstrate that using conventional water ultrafiltration results in predominately low molecular weight peptides (FIG. 5A), while buffer ultrafiltration results in purified keratin nanomaterials (FIG. 5B).

Example 5

Size Exclusion Chromatography of Keratin Samples Extracted by a Reductive Solution of $Na_2S$/Urea A sample of human Chinese hair was obtained from a commercial vendor and used as received. 100 grams of hair was placed into a 4 L solution of 0.042M sodium sulfide and 1M urea (pH 12.6) and shaken at 150 rpm for 1.5 hours at 37° C. Following the incubation, the hair was recovered by sieve and the extraction solution retained. The hair fibers were then further extracted with 1 L purified water by shaking at 150 rpm for 30 minutes at 37° C. The hair was recovered by sieve and discarded, while the extraction solutions were retained and pooled. The crude keratin extract was then clarified of particulate matter by centrifugation through a solids separator running at 30,000 rpm followed by filtration through a membrane with a 20-25 µm average pore size. Keratin nanomaterials were obtained from this clarified crude keratin extract by ultrafiltration using a 100 kDa NLMWCO polysulfone, spiral wound filter cartridge. Ultrafiltration was conducted on half of the extract using a buffer consisting of 5 mM disodium phosphate and 150 mM sodium sulfide at pH 9A for 10 volume washes followed by 3 volume washes against purified water. The purified keratin nanomaterial solution was concentrated, titrated to pH 8.5, frozen and freeze dried to produce a keratin nanomaterial powder. The keratin nanomaterial powder was utilized to create stable hydrogels and scaffolds.

Samples from both the buffer ultrafiltration and a replicate extraction process with conventional water ultrafiltration were analyzed using SEC to assess the presence of purified keratin nanomaterials. Samples were analyzed on a Dionex manual injector with a 20-microliter loop and Ultimate 3000 UV/Vis detector set at 280 nm. Data collection was performed using the Chromeleon v6.8 chromatography software. SEC chromatograms demonstrate that regardless of the extraction process utilized, using conventional water ultrafiltration results in predominately low molecular weight peptides, while buffer ultrafiltration results in purified keratin nanomaterials.

Example 6

Production of Keratin Nanomaterial Hydrogels

A sample of human Chinese hair was obtained from a commercial vendor and used as received. 100 grams of hair fibers was placed into 2 L of 2 wt/vol percent peracetic acid and shaken at 150 rpm for 8 hours at 37° C. The oxidized hair was recovered by sieve and extracted with 4 L of 100 mM tris base by shaking at 150 rpm for 16 hours at 37° C. The hair was recovered by sieve, the extract solution was retained, and the hair fibers further extracted with 4 L of purified water by shaking at 150 rpm for 2 hours at 37° C. The hair was recovered by sieve and discarded, and the extract solution retained. Both extract solutions were combined to form a solution of crude keratin extract, which was clarified of particulate matter by centrifugation through a solids separator running at 40,000 rpm followed by filtration through a membrane with 20-25 micrometer average pore size. Keratin nanomaterials were obtained from this crude solution by ultrafiltration using a 100 kilo Dalton NLMWCO polysulfone, spiral wound filter cartridge. The buffer used consisted of 10 mM disodium phosphate plus 100 mM sodium chloride at approximately pH 7.4 and the ultrafiltration was conducted for 5 volume washes. A second phase of ultrafiltration was conducted with 5 volume washes of purified water. The purified keratin nanomaterial solution was concentrated, titrated to pH 7.4, frozen, and freeze dried to produce a keratin nanomaterial powder. The dried keratin nanomaterial powder was reconstituted to viscous hydrogels at 10, 8, and 5 wt/wt percent keratin to purified water. All three hydrogels resisted flow and were intact following incubation at 37° C. for 24 hours.

It will be understood that the Specification and Examples are illustrative of the present embodiments and that other embodiments within the spirit and scope of the claimed embodiments will suggest themselves to those skilled in the art. Although this disclosure has been described in connection with specific forms and embodiments thereof, it would be appreciated that various modifications other than those discussed above may be resorted to without departing from the spirit or scope of the embodiments as defined in the appended claims. For example, equivalents may be substituted for those specifically described, and in certain cases, particular applications of steps may be reversed or interposed all without departing from the spirit or scope for the disclosed embodiments as described in the appended claims. Additionally, one skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features.

It is noted in particular that where a range of values is provided in this specification, each value between the upper and lower limits of that range is also specifically disclosed. The upper and lower limits of these smaller ranges may independently be included or excluded in the range as well. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A keratin nanomaterial comprising two (2) Type I and Type II monomer pairs, wherein the nanomaterial has a molecular size of approximately 50 nm in length and approximately 1 nm to 5 nm in diameter.

2. The keratin nanomaterial of claim 1 comprising a mixture of dimers and tetramers.

3. The keratin nanomaterial of claim 1 comprising a molecular complex essentially devoid of other proteins and/or peptides.

4. The keratin nanomaterial of claim 1, wherein the nanomaterial has a molecular weight of greater than 100 kDa.

5. The keratin nanomaterial of claim 1, wherein the nanomaterial has a molecular weight of greater than 200 kDa.

6. A keratin nanomaterial comprising two (2) Type I and Type II monomer pairs, wherein the nanomaterial has a molecular size of approximately 50 nm to 100 nm in length and approximately 5 nm to 10 nm in diameter.

7. A method for obtaining keratin nanomaterials comprising the following steps:
   a. obtaining a solution of keratins;
   b. processing the solution of keratins by ultrafiltration with buffer solution containing phosphate; and
   c. and further processing said solution by removing water to form a solid keratin nanomaterial of claim 1 or claim 6.

8. The method of claim 7, wherein the ultrafiltration is conducted with a NLMWCO membrane of 30 kDa.

9. The method of claim 7, wherein the ultrafiltration is conducted with a NLMWCO membrane of 100 kDa.

10. The method of claim 7, wherein the ultrafiltration is conducted with a NLMWCO membrane of 200 kDa.

11. The method of claim 7, wherein the ultrafiltration is conducted with a NLMWCO membrane of 300 kDa.

12. The method of claim 7, wherein the buffer solution containing phosphate comprises sodium phosphate.

13. The method of claim 7, wherein the buffer solution containing phosphate comprises monosodium phosphate.

14. The method of claim 7, wherein the buffer solution containing phosphate comprises disodium phosphate.

15. The method of claim 7, wherein the buffer solution containing phosphate comprises potassium phosphate.

16. The method of claim 7, wherein the buffer solution containing phosphate comprises monopotassium phosphate.

17. The method of claim 7, wherein the buffer solution containing phosphate comprises dipotassium phosphate.

18. The method of claim 7, wherein the buffer solution further comprises potassium chloride.

19. The keratin nanomaterial of claim 6 comprising a mixture of dimers and tetramers.

20. The keratin nanomaterial of claim 6 comprising a molecular complex essentially devoid of other proteins and/or peptides.

21. The keratin nanomaterial of claim 6, wherein the nanomaterial has a molecular weight of greater than 100 kDa.

22. The keratin nanomaterial of claim 6, wherein the nanomaterial has a molecular weight of greater than 200 kDa.

* * * * *